United States Patent
Tsai et al.

(10) Patent No.: US 11,969,448 B2
(45) Date of Patent: Apr. 30, 2024

(54) METHOD FOR IMPROVING AN EFFECT OF CHEMOTHERAPEUTIC DRUG OF GEMCITABINE ON INHIBITING PANCREATIC CANCER AND IMPROVING SIDE EFFECT OF CHEMOTHERAPEUTIC DRUG OF GEMCITABINE

(71) Applicant: GENMONT BIOTECH INC., Tainan (TW)

(72) Inventors: Wan-Hua Tsai, Kaohsiung (TW); I-ling Hsu, Tainan (TW); Shan-ju Hsu, Tainan (TW); Wen-ling Yeh, Tainan (TW); Ming-shiou Jan, Taichung (TW); Wee-wei Chieng, Tainan (TW); Li-jin Hsu, Tainan (TW); Ying-chun Lai, Taichung (TW)

(73) Assignee: GENMONT BIOTECH INC., Tainan (TW)

( * ) Notice: Subject to any disclaimer, the term of this patent is extended or adjusted under 35 U.S.C. 154(b) by 43 days.

(21) Appl. No.: 17/317,928

(22) Filed: May 12, 2021

(65) Prior Publication Data

US 2022/0031775 A1 Feb. 3, 2022

Related U.S. Application Data

(60) Provisional application No. 63/057,940, filed on Jul. 29, 2020.

(51) Int. Cl.
*A61K 35/747* (2015.01)
*A61P 35/00* (2006.01)

(52) U.S. Cl.
CPC ............ *A61K 35/747* (2013.01); *A61P 35/00* (2018.01)

(58) Field of Classification Search
CPC .............. A61K 35/747; A61K 31/7068; A61K 35/744; A61P 35/00; A61P 1/18; A61P 39/00; C12N 1/20
See application file for complete search history.

(56) References Cited

U.S. PATENT DOCUMENTS 10,632,160 B2 * 4/2020 Chen ....................... A61P 35/00
2011/0229447 A1 9/2011 Schiffrin et al.
(Continued)

FOREIGN PATENT DOCUMENTS

CN 103355668 A 10/2013
CN 104398538 A 3/2015
(Continued)

OTHER PUBLICATIONS

Carmichael, J. The role of gemcitabine in the treatment of other tumours. Br J Cancer 78 (Suppl 3), 21-25 (1998). https://doi.org/10.1038/bjc.1998.750 (Year: 1998).*
(Continued)

*Primary Examiner* — Thomas J. Visone
(74) *Attorney, Agent, or Firm* — Rivka Friedman

(57) ABSTRACT

A probiotic composition for improving an effect of a chemotherapeutic drug of Gemcitabine on inhibiting pancreatic cancer is disclosed in the present disclosure. The probiotic composition comprises an effective amount of *Lactobacillus paracasei* GMNL-133, an effective amount of *Lactobacillus reuteri* GMNL-89, and a pharmaceutically acceptable carrier, wherein the *Lactobacillus paracasei* GMNL-133 was deposited in the China Center for Type Culture Collection on Sep. 26, 2011 under an accession number CCTCC NO. M 2011331, and the *Lactobacillus reuteri* GMNL-89 was deposited in the China Center for Type Culture Collection on Nov. 19, 2007 under an accession number CCTCC NO. M 207154. A method for improving the effect of the chemo-
(Continued)

therapeutic drug of Gemcitabine on inhibiting pancreatic cancer is further disclosed in the present disclosure.

2 Claims, 8 Drawing Sheets

Specification includes a Sequence Listing.

(56) References Cited

U.S. PATENT DOCUMENTS

| | | |
|---|---|---|
| 2015/0238548 A1 | 8/2015 | Huang et al. |
| 2022/0211779 A1 | 7/2022 | Jeong et al. |

FOREIGN PATENT DOCUMENTS

| | | | |
|---|---|---|---|
| CN | 108707557 A | * 10/2018 | ........... A61K 35/747 |
| CN | 108707557 A | 10/2018 | |
| KR | 102049700 B1 | 11/2019 | |
| WO | WO-2010033425 A2 | * 3/2010 | ............. A23L 33/40 |
| WO | 2019169179 A1 | 9/2019 | |

OTHER PUBLICATIONS

Flórez AB, Sierra M, Ruas-Madiedo P, Mayo B. Susceptibility of lactic acid bacteria, bifidobacteria and other bacteria of intestinal origin to chemotherapeutic agents. Int J Antimicrob Agents. Nov. 2016;48(5):547-550. (Year: 2016).*

Carmichael, J. The role of gemcitabine in the treatment of other tumours. Br J Cancer 78 (Suppl 3), 21-25 (1998). https://doi.org/10.1038/bjc.1998.750 (Year: 1998) (Year: 1998).*

Bindels, L., Neyrinck, A., Claus, S. et al. Synbiotic approach restores intestinal homeostasis and prolongs survival in leukaemic mice with cachexia. ISME J 10, 1456-1470 (2016). https://doi.org/10.1038/ismej.2015.209 (Year: 2015).*

Flórez AB, Sierra M, Ruas-Madiedo P, Mayo B. Susceptibility of lactic acid bacteria, bifidobacteria and other bacteria of intestinal origin to chemotherapeutic agents. Int J Antimicrob Agents. Nov. 2016;48(5):547-550. (Year: 2016) (Year: 2016).*

Hsu, T., Huang, C., Liu, C., Hsu, K., Chen, Y., & Tzang, B. (2017). Lactobacillus paracasei GMNL-32, Lactobacillus reuteri GMNL-89 and L. reuteri GMNL-263 ameliorate hepatic injuries in lupus-prone mice. British Journal of Nutrition, 117(8), 1066-1074. doi: 10.1017/S0007114517001039 (Year: 2017).*

Amrutkar et al., Cancers, 9(157):1-23 (2017) (Year: 2017).*

Da Silva et al., J. Cachexia Sarcopenia Muscle, 11:619-635 (2020) (Year: 2020).*

An et al., J. Microbiol., 58(11):967-977 (2020) (Year: 2020).*

Chang et al., Food Funct., 10:7634-7344 (2019) (Year: 2019).*

Choy et al., Expert Rev. Mol. Diag., 18(12):1005-1009 (2018) (Year: 2018).*

Geller et al., Science, 357:1156-1160 (2017) (Year: 2017).*

Gori et al., Crit. Rev. Oncol. Hematol., 143:139-147 (2019) (Year: 2019).*

Mao et al., J. Immunol. Res., 4092472:1-9 (2020) (Year: 2020).*

Montalban-Arques et al., EBioMedic., 48:648-655 (2019) (Year: 2019).*

Nowak et al., Crit. Rev. Food Sci. Nutr., 59(21):3456-3467 (2019) (Year: 2019).*

Panebianco et al., Microbiome, 6(92):1-13 (2018) (Year: 2018).*

Panebianco et al., Can. Chemother. Pharmacol., 81:773-782 (2018) (Year: 2018).*

Pizano et al., (Integr. Medic., 17(2):32-44 (2018) (Year: 2018).*

"Susceptibility of lactic acid bacteria, bifidobacteria and other bacteria of intestinal origin to chemotherapeutic agents" □Ana B Flórez et al.□Int J Antimicrob Agents□vol. 48, Issue 5, pp. 547-550.

Practical Surgical Oncology, Zhimin Shao, pp. 516-517, Fudan University Press.

* cited by examiner

METHOD FOR IMPROVING AN EFFECT OF CHEMOTHERAPEUTIC DRUG OF GEMCITABINE ON INHIBITING PANCREATIC CANCER AND IMPROVING SIDE EFFECT OF CHEMOTHERAPEUTIC DRUG OF GEMCITABINE

CROSS-REFERENCE TO RELATED APPLICATIONS

The present application claims the benefit of U.S. provisional patent application No. 63/057,940 filed Jul. 29, 2020, the disclosure of which is incorporated herein by reference.

SEQUENCE LISTING STATEMENT

The ASCII file, entitled TP201997-US sequence final (ASCII), created on May 12, 2021, comprising 2351 bytes, submitted concurrently with the filing of this application is incorporated herein by reference.

FIELD OF INVENTION

The present disclosure relates to a probiotic composition of *Lactobacillus paracasei* GMNL-133 (*L. paracasei* GMNL-133) and *Lactobacillus reuteri* GMNL-89 (*L. reuteri* GMNL-89), and in particular to a method for improving an effect of a chemotherapeutic drug of Gemcitabine on inhibiting pancreatic cancer.

BACKGROUND OF INVENTION

Pancreatic cancer is known as the "quiet killer" due to no symptom in early stage, difficult diagnosis and rapid deterioration. It is one of the lethal cancers in recent years with less than 10% of 5-year survival rate. According to a survey conducted by GLOBOCAN in 2018, pancreatic cancer is the seventh leading cause of cancer deaths in the world, the third leading cause of cancer deaths in the United States in 2019, and the eighth of the top ten local cancer deaths in Taiwan. The causes of pancreatic cancer are related to heredity, genetic variation, age, lifestyle and working environments.

85% of pancreatic cancers are pancreatic ductal adenocarcinoma (PDAC) which is a highly invasive cancer. The dominant sites for pancreatic ductal adenocarcinoma are the head (60 to 70%), body and tail (20 to 25%) of the pancreas. In addition, 90% of pancreatic cancers have point mutations in the oncogene Kras$^{G12D}$. The best treatment for pancreatic cancers is surgical resection combined with chemotherapy. However, since only patients with carcinoma in situ (10 to 20%) can receive surgery, the treatment is mainly chemotherapy.

Chemotherapeutic drugs commonly used for pancreatic cancer include Gemcitabine (Gemzar), 5-fluorouracil (5-FU), Oxaliplatin (Eloxatin), Albumin-bound paclitaxel (Abraxane), Capecitabine (Xeloda), Cisplatin and Irinotecan (Campotosar), wherein Gemcitabine is the standard first-line chemotherapeutic drug for advanced pancreatic cancer, and the 5-year survival rate of patients can be increased to 30%. Although the chemotherapeutic drug of Gemcitabine can effectively kill cancer cells, it is often accompanied by strong side effects, such as nausea, vomiting, anemia, low white blood cell count, low platelet count, elevated liver function index, fever, proteinuria, hematuria, dyspnea and edema. Others possible side effects include rash, pruritus, loss of appetite, hair loss, headache, diarrhea and constipation, etc., which cause a serious impact on the quality of life and survival rate of patients.

Previous studies have found that oral probiotics have many effects, including balancing the intestinal microbiota, improving the gastrointestinal barrier, and inhibiting the formation of potential pathogenic bacteria or cancer in the intestine. Recent studies have found that the microbiota of the intestine is related to the occurrence and progression of colorectal cancer, liver cancer and pancreatic cancer. Probiotics can improve the survival rate of patients through mechanisms such as inhibiting tumor growth, delaying the progress of cancer, regulating immunity and reducing intestinal damage.

Many studies have pointed out that probiotics can improve the effect of chemotherapy. For example, in cell experiments of colorectal cancer, the extract of *Lactobacillus paracasei* (NTU 101) can increase the toxicity of chemotherapeutic drugs to kill cancer cells, inhibit the migration of cancer cells, and enhance the activity of macrophages (Chang Cy et al., Food Funct 2019, 10:7634-44; Chang Cy et al., J Agric Food Chem, 66:5549-55). For example, in experiments on mice with colorectal cancer, *Lactobacillus paracasei* (NTU 101) can promote appetite in chemotherapy-treated mice, improve weight loss, reduce inflammatory factors and oxidative stress in the body, and increase the effect of chemotherapeutic drugs on tumor growth (Chang C Y et al., Journal of Functional Foods 2019, 55:36-47; Zhang Jiayuan, 2019). For example, in experiments on mice with liver cancer, the fermentation supernatant of *Lactobacillus reuteri* combined with chemotherapeutic drugs can induce cancer cells to necrosis and strengthen the ability of the chemotherapeutic drugs to inhibit cancer cells (Alem M et al., J Cancer Res Ther 2019, 15:176-84). In clinical trials, oral probiotic *Lactobacillus reuteri* can alleviate the symptoms of acute proctitis caused by radiotherapy in patients with pancreatic cancer and improve the quality of life. In addition, cancer treatments combined with probiotics can also reduce the side effects of the cancer treatments. For example, in the experiments of chemotherapeutic drugs of Irinotecan causing diarrhea in rats, the multi-strain *lactobacillus* formula containing *Lactobacillus paracasei* can improve severe diarrhea and weight loss caused by chemotherapy (Bowen J M et al., Cancer Biol Ther 2007, 6: 1449-54). Therefore, probiotics are regarded as a new strategy to improve the side effects of chemotherapy and cancer prevention and treatment.

*Lactobacillus paracasei* and *Lactobacillus reuteri* are lactic acid bacteria with considerable anticancer potential. For example, *Lactobacillus paracasei* GMNL-133 can inhibit overexpression of T helper 2 cells by stimulating pancreatic cells to produce interferon-γ, and at the same time reduce the proliferation of B cells, thereby achieving the effect of regulating immunity. *Lactobacillus reuteri* has the ability to produce antibacterial substances, inhibit the colonization of pathogenic bacteria and regulate immunity, and is considered to be a strain that can be used to prevent or treat inflammatory diseases.

SUMMARY OF INVENTION

Technical Problems

A purpose of the present disclosure is to provide a probiotic composition for improving an effect of a chemotherapeutic drug of Gemcitabine on inhibiting pancreatic cancer, which can treat cancer while reducing the side effects of chemotherapy.

Technical Solutions

In order to achieve the foregoing purpose of the present disclosure, the present disclosure provides a probiotic composition for improving an effect of a chemotherapeutic drug of Gemcitabine on inhibiting pancreatic cancer, comprising: an effective amount of *Lactobacillus paracasei* GMNL-133, an effective amount of *Lactobacillus reuteri* GMNL-89, and a pharmaceutically acceptable carrier, wherein the *Lactobacillus paracasei* GMNL-133 was deposited in the China Center for Type Culture Collection (CCTCC) located at Wuhan University, Wuhan 430072 P.R. China on Sep. 26, 2011 under an accession number CCTCC NO. M 2011331 under the Budapest Treaty, and the *Lactobacillus reuteri* GMNL-89 was deposited in the China Center for Type Culture Collection located at Wuhan University, Wuhan 430072 P.R. China on Nov. 19, 2007 under an accession number CCTCC NO. M 207154 under the Budapest Treaty.

According to an embodiment of the present disclosure, a ratio of a number of bacteria of the *Lactobacillus paracasei* GMNL-133 to a number of bacteria of the *Lactobacillus reuteri* GMNL-89 ranges from 1:0.1 to 1:1.

In order to achieve the foregoing purpose of the present disclosure, the present disclosure further provides a method for improving an effect of a chemotherapeutic drug of Gemcitabine on inhibiting pancreatic cancer, comprising a step of administering the above-mentioned probiotic composition to a subject in need.

According to an embodiment of the present disclosure, a ratio of a number of bacteria of the *Lactobacillus paracasei* GMNL-133 to a number of bacteria of the *Lactobacillus reuteri* GMNL-89 ranges from 1:0.1 to 1:1.

According to an embodiment of the present disclosure, the *Lactobacillus paracasei* GMNL-133 in the probiotic composition is administered at a dose of $4\times10^9$ to $4\times10^{10}$ cfu/60 kg of body weight per day to a subject in need of improving the effect of the chemotherapeutic drug of Gemcitabine on inhibiting pancreatic cancer, and the *Lactobacillus reuteri* GMNL-89 in the probiotic composition is administered at a dose of $4\times10^9$ to $4\times10^{10}$ cfu/60 kg of body weight per day to the subject in need of improving the effect of the chemotherapeutic drug of Gemcitabine on inhibiting pancreatic cancer.

According to an embodiment of the present disclosure, the *Lactobacillus paracasei* GMNL-133 in the probiotic composition is administered at a dose of $4\times10^9$ to $4\times10^{10}$ cfu/60 kg of body weight per day to a subject in need of improving the effect of the chemotherapeutic drug of Gemcitabine on inhibiting pancreatic cancer, and the *Lactobacillus reuteri* GMNL-89 in the probiotic composition is administered at a dose of $4\times10^8$ to $4\times10^9$ cfu/60 kg of body weight per day to the subject in need of improving the effect of the chemotherapeutic drug of Gemcitabine on inhibiting pancreatic cancer.

In order to achieve the foregoing purpose of the present disclosure, the present disclosure further provides a method for improving a side effect of a chemotherapeutic drug of Gemcitabine, comprising a step of administering the above-mentioned probiotic composition to a subject in need.

According to an embodiment of the present disclosure, a ratio of a number of bacteria of the *Lactobacillus paracasei* GMNL-133 to a number of bacteria of the *Lactobacillus reuteri* GMNL-89 ranges from 1:0.1 to 1:1.

According to an embodiment of the present disclosure, the *Lactobacillus paracasei* GMNL-133 in the probiotic composition is administered at a dose of $4\times10^9$ to $4\times10^{10}$ cfu/60 kg of body weight per day to a subject in need of improving the side effect of the chemotherapeutic drug of Gemcitabine, and the *Lactobacillus reuteri* GMNL-89 in the probiotic composition is administered at a dose of $4\times10^9$ to $4\times10^{10}$ cfu/60 kg of body weight per day to the subject in need of improving the side effect of the chemotherapeutic drug of Gemcitabine.

According to an embodiment of the present disclosure, the *Lactobacillus paracasei* GMNL-133 in the probiotic composition is administered at a dose of $4\times10^9$ to $4\times10^{10}$ cfu/60 kg of body weight per day to a subject in need of improving the side effect of the chemotherapeutic drug of Gemcitabine, and the *Lactobacillus reuteri* GMNL-89 in the probiotic composition is administered at a dose of $4\times10^8$ to $4\times10^8$ cfu/60 kg of body weight per day to the subject in need of improving the side effect of the chemotherapeutic drug of Gemcitabine.

Beneficial Effects

The probiotic composition of the present disclosure not only has the effect of treating pancreatic cancer by itself, but also can improve the anticancer effect of the chemotherapeutic drug of Gemcitabine when used in combination with the chemotherapeutic drug of Gemcitabine. Moreover, the probiotic composition of the present disclosure can effectively improve the side effects caused by the chemotherapeutic drug of Gemcitabine in the treatment of pancreatic cancer, and thus can increase body weight, muscle weight, white blood cells, and reduce liver function indexes of AST and ALT.

DESCRIPTION OF DRAWINGS

In order to more clearly illustrate the above contents of the present disclosure, the following is a detailed description of the preferred embodiments with reference to the accompanying drawings.

DETAILED DESCRIPTION OF PREFERRED EMBODIMENTS

Figure 1:
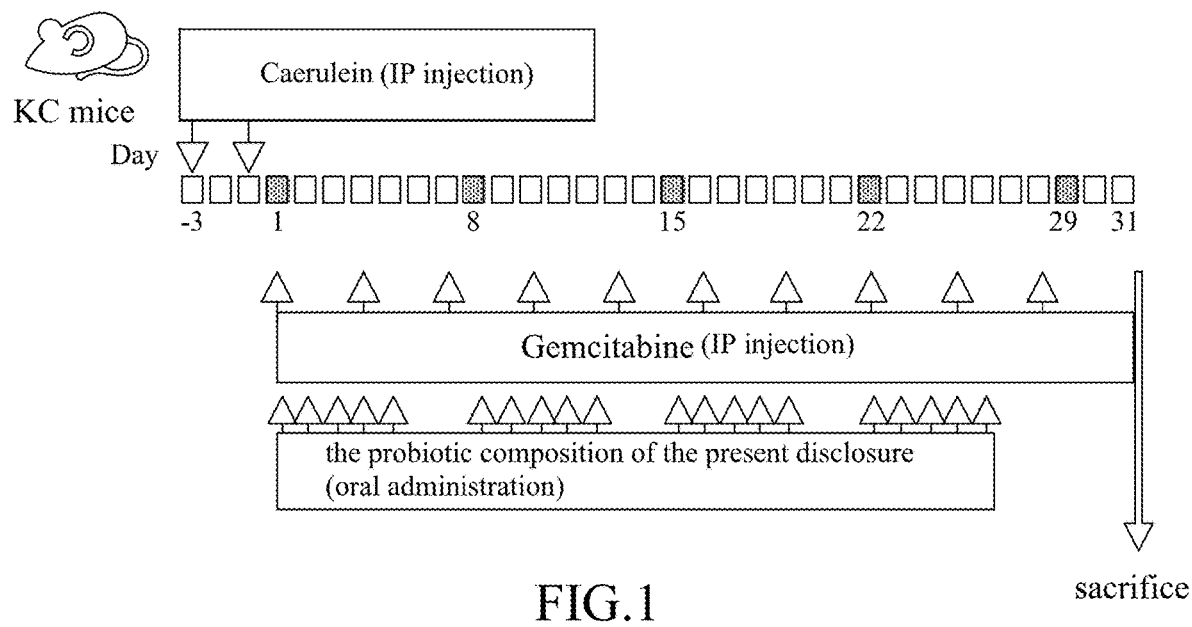
FIG. 1 is a schematic diagram of an experimental design of mice with pancreatic cancer in the present experiment.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As used herein, the singular form "a", "an" and "the" include plural references unless the context clearly dictates otherwise. The numerical range (such as 10% to 11% of A) includes the upper and lower limits (i.e., 10%≤A≤11%) unless otherwise specified. If the numerical range does not define the lower limit (such as less than 0.2% of B, or below 0.2% of B), it means that the lower limit may be 0 (i.e., 0%≤B≤0.2%). The above terms are made for the purposes of describing and illustrating the present disclosure and should not be taken in a limiting sense.

The present disclosure provides a probiotic composition for improving an effect of a chemotherapeutic drug of Gemcitabine on inhibiting pancreatic cancer, comprising: an effective amount of *Lactobacillus paracasei* GMNL-133, an effective amount of *Lactobacillus reuteri* GMNL-89, and a pharmaceutically acceptable carrier, wherein the *Lactobacillus paracasei* GMNL-133 was deposited in the China Center for Type Culture Collection (CCTCC) located at Wuhan University, Wuhan 430072 P.R. China on Sep. 26, 2011 under an accession number CCTCC NO. M 2011331 under the Budapest Treaty, and the *Lactobacillus reuteri* GMNL-89 was deposited in the China Center for Type Culture Collection located at Wuhan University, Wuhan 430072 P.R. China on Nov. 19, 2007 under an accession number CCTCC NO. M 207154 under the Budapest Treaty.

Specifically, a ratio of a number of bacteria of the *Lactobacillus paracasei* GMNL-133 to a number of bacteria of the *Lactobacillus reuteri* GMNL-89 ranges from 1:0.1 to 1:1, for example, 1:0.1, 1:0.2, 1:0.3, 1:0.4, 1:05, 1:0.6, 1:0.7, 1:0.8, 1:0.9, 1:1.

The present disclosure further provides a method for improving an effect of a chemotherapeutic drug of Gemcitabine on inhibiting pancreatic cancer, comprising a step of administering the above-mentioned probiotic composition to a subject in need.

Specifically, a ratio of a number of bacteria of the *Lactobacillus paracasei* GMNL-133 to a number of bacteria of the *Lactobacillus reuteri* GMNL-89 ranges from 1:0.1 to 1:1. In a case where a ratio of a number of bacteria of the *Lactobacillus paracasei* GMNL-133 to the *Lactobacillus reuteri* GMNL-89 is 1:0.1 and the subject in need of improving the effect of the chemotherapeutic drug of Gemcitabine on inhibiting pancreatic cancer is a human, the therapeutically effective amount of the *Lactobacillus paracasei* GMNL-133 per day for adults is $4\times10^9$ to $4\times10^{10}$ cfu/60 kg of body weight per day, and the therapeutically effective amount of the *Lactobacillus reuteri* GMNL-89 per day for adults is $4\times10^9$ to $4\times10^{10}$ cfu/60 kg of body weight per day in the composition administered to the subject in need of improving the effect of the chemotherapeutic drug of Gemcitabine on inhibiting pancreatic cancer. In a case where a ratio of a number of bacteria of the *Lactobacillus paracasei* GMNL-133 to the *Lactobacillus reuteri* GMNL-89 is 1:0.1 and the subject in need of improving the effect of the chemotherapeutic drug of Gemcitabine on inhibiting pancreatic cancer is a human, the therapeutically effective amount of the *Lactobacillus paracasei* GMNL-133 per day for adults is $4\times10^9$ to $4\times10^{10}$ cfu/60 kg of body weight per day, and the therapeutically effective amount of the *Lactobacillus reuteri* GMNL-89 per day for adults is $4\times10^8$ to $4\times10^9$ cfu/60 kg of body weight per day in the composition administered to the subject in need of improving the effect of the chemotherapeutic drug of Gemcitabine on inhibiting pancreatic cancer.

The present disclosure further provides a method for improving a side effect of a chemotherapeutic drug of Gemcitabine, comprising a step of administering the above-mentioned probiotic composition to a subject in need.

Specifically, a ratio of a number of bacteria of the *Lactobacillus paracasei* GMNL-133 to the *Lactobacillus reuteri* GMNL-89 ranges from 1:0.1 to 1:1. In a case where a ratio of a number of bacteria of the *Lactobacillus paracasei* GMNL-133 to the *Lactobacillus reuteri* GMNL-89 is 1:1, and a subject in need of improving the side effect of the chemotherapeutic drug of Gemcitabine is a human, the therapeutically effective amount of the *Lactobacillus paracasei* GMNL-133 per day for adults is $4\times10^9$ to $4\times10^{10}$ cfu/60 kg of body weight per day, and the therapeutically effective amount of the *Lactobacillus reuteri* GMNL-89 for adults is $4\times10^9$ to $4\times10^{10}$ cfu/60 kg of body weight per day in the composition administered to the subject in need of improving the side effect of the chemotherapeutic drug of Gemcitabine. In a case where a ratio of a number of bacteria of the *Lactobacillus paracasei* GMNL-133 to the *Lactobacillus reuteri* GMNL-89 is 1:0.1 and the subject in need of improving the side effect of the chemotherapeutic drug of Gemcitabine is a human, the therapeutically effective amount of the *Lactobacillus paracasei* GMNL-133 per day for adults is $4\times10^9$ to $4\times10^{10}$ cfu/60 kg of body weight per day, and the therapeutically effective amount of the *Lactobacillus reuteri* GMNL-89 per day for adults is $4\times10^8$ to $4\times10^9$ cfu/60 kg of body weight per day in the composition administered to the subject in need of improving the side effect of the chemotherapeutic drug of Gemcitabine.

The pharmaceutically acceptable carrier may include one or more agents selected from the group consisting of solvents, stabilizers, emulsifiers, suspending agents, decomposing agents, flavoring agents, binding agents, excipients, cosolvents, chelating agents, diluents, gelling agents, preservatives, lubricants and surfactants.

The term "administering" the composition to a subject refers to directly administering the composition to the subject, and the composition can be administered by professional medical personnel, or on the subject's own.

The term "cancer" herein includes the broader term "abnormal cell proliferation", which is also called "excessive cell proliferation" or "proliferative disease". Examples of diseases associated with abnormal cell proliferation include metastatic tumors, malignant tumors, benign tumors, cancers, precancerous lesions, hyperplasia, and polyps.

The term "subject" herein refers to mammals that need to improve the effect of Gemcitabine on inhibiting pancreatic cancer. Generally, the "subject" is human. However, in other embodiments, the "subject" may be a non-human mammal, such as a non-human primate, dog, cat, cow, horse, rabbit, pig, etc. In the embodiment of the present disclosure, the "subject" treated by the probiotic composition of the present disclosure is mice. Certainly, the present disclosure is not limited to this. In other embodiments, the "subject" treated by the probiotic composition herein may be, for example, animals commonly used for screening, characterizing and evaluating compositions (compounds, drugs, probiotics) and treatments.

The term "treatment" refers to methods used to obtain beneficial or desired results (including clinical results). For the purpose of the present disclosure, beneficial or desired clinical results include, but are not limited to, reduction or improvement of one or more symptoms, reduction of the disease degree, stability of the disease state (i.e., no deterioration), prevention of the disease spread, delay or slowing of the disease progress, and improvement, alleviation and remission (partial or complete remission) of the disease state.

The term "treatment" may also mean prolonged survival period if compared with the expected survival period without treatment.

The term "therapeutically effective amount" refers to an amount that is effective to achieve the desired therapeutic result at the necessary dose and within the necessary period. "Therapeutically effective amount" can vary depending on various factors, such as the disease state, the age, the sex, and the weight of the individual patient, and the ability of the probiotic composition of the present disclosure to cause the desired response in the individual. "Therapeutically effective amount" is also an amount in which the beneficial effects of the treatment exceed any toxic or harmful effects of the treatment. The therapeutically effective amount of the tumor therapy can also be measured by the ability to stabilize the progression of the disease, to reduce the size of the tumor, or to eliminate the tumor completely. The ability of the treatment to inhibit cancer can be evaluated in an animal model system that predicts efficacy in human tumors. Alternatively, the characteristic of the composition can be evaluated by examining an ability of the compound to inhibit cell growth or induce apoptosis using in vitro assays known to those skilled in the art. A skilled practitioner will be able to determine these amounts based on the physique of patients, the severity of symptoms of patients, and specific routes of administration.

The probiotic composition of the present disclosure can be prepared into a variety of dosage forms, including but not limited to: solutions, emulsions, suspensions, powders, pastilles, pills, lozenges, tablets, chewing gums, capsules, and other dosage forms similar to or applicable to the probiotic composition of the present disclosure.

In order to verify that the probiotic composition of the present disclosure can improve the effect of the chemotherapeutic drug of Gemcitabine on inhibiting pancreatic cancer, the following animal experiments were performed. In the animal model, since symptoms of mice are close to clinical symptoms of humans, the mice can be used to evaluate and simulate the effects of the probiotic composition of the present disclosure when used in humans.

In the following experiments, the experimental methods without specific conditions are selected according to conventional methods and conditions, or according to the instructions of the kit.

Evaluation and Identification of Strains:

Characteristics of *Lactobacillus paracasei* GMNL-133:

The source of the *Lactobacillus paracasei* GMNL-133 is the human small intestine.

The *Lactobacillus paracasei* GMNL-133 was seeded on the agar medium (De Man, Rogosa and Sharpe, MRS) and cultured at 37° C. for 48 hours, and then the morphology of the *Lactobacillus paracasei* GMNL-133 was observed. The appearance characteristics of the colony: complete edges, 2.5 mm×2.5 mm of the average size, milky white, and smooth and raised surface. The Gram staining result: positive. Type: rod-shaped (bacilli). Spore formation: None. Mobility: None.

The physiological characteristics of the *Lactobacillus paracasei* GMNL-133 are as follows: growth temperature: 35° C. to 40° C.; growth pH: 4.0 to 7.0; oxygen effect: facultative anaerobic.

In addition, after the total RNA of the *Lactobacillus paracasei* GMNL-133 was extracted by the conventional method, the partial sequence of the 16S rRNA gene was amplified by the primer pairs shown as SEQ ID NO: 1 and SEQ ID NO: 2, wherein the forward primer is PAF primer, and the downstream primer is 536R primer. The obtained nucleic acid fragment is shown as SEQ ID NO: 3. The method for extracting total RNA is well known to those with ordinary knowledge in the technical field of the present disclosure, and will not be described here.

The nucleic acid fragment has 100% sequence identity compared with the 16S rRNA gene sequence of two *Lactobacillus paracasei* (GenBank numbers: NR_041054.1, NR_025880.1) in the GenBank of National Center for Biotechnology Information (NCBI). In addition, the obtained nucleic acid fragment shown as SEQ ID NO: 3 also has 99% sequence identity with the 16S rRNA gene sequences of the other two *Lactobacillus paracasei* (GenBank numbers: NR_113337.1, NR_117987.1). Thus, the nucleic acid fragment is confirmed as *Lactobacillus paracasei*.

Characteristics of *Lactobacillus reuteri* GMNL-89:

The source of the *Lactobacillus reuteri* (GMNL-89) is the human small intestine.

The *Lactobacillus reuteri* GMNL-89 was seeded on the MRS agar culture medium and cultured at 37° C. for 48 hours, and then the morphology of the *Lactobacillus reuteri* GMNL-89 was observed. The appearance characteristics of the colony: complete edges, 2.5 mm×2.5 mm of the average size, milky white, and smooth and raised surface. The Gram staining result: positive. Type: rod-shaped (bacilli). Spore formation: None. Mobility: None.

The physiological characteristics of the *Lactobacillus reuteri* GMNL-89 are as follows: growth temperature: 35° C. to 40° C.; growth pH: 4.0 to 7.0; oxygen effect: facultative anaerobic.

In addition, after the total RNA of the *Lactobacillus reuteri* GMNL-89 was extracted by the conventional method, the partial sequence of the 16S rRNA gene was amplified by the primer pairs shown as SEQ ID NO: 1 and SEQ ID NO: 2. The obtained nucleic acid fragment is shown as SEQ ID NO: 4. The method for extracting total RNA is well known to those with ordinary knowledge in the technical field of the present disclosure, and will not be described here.

The nucleic acid fragment has 99% sequence identity compared with the 16S rRNA gene sequence of two *Lactobacillus reuteri* in the NCBI gene bank (GenBank numbers: NR_075036.1, NR_113820.1, NR_119069.1, wherein NR_075036.1 and NR_119069.1 are the same strains). Thus, the nucleic acid fragment is confirmed as *Lactobacillus reuteri*.

Experimental Method:

Experimental Animals:

In the experiment, a 12-week-old LSL-Kras$^{G12D/-}$-Pdx-1-Cre (KC) gene transgenic mouse was used to simulate a mouse model of pancreatic cancer. The national laboratory animal center of National Applied Research Laboratories was entrusted to introduce the experimental animals from the Frederick National Laboratory for cancer research, and then conduct breeding, reproducing and embryo freezing, and then the experimental animals are bred in the animal center attached to Chung Shan Medical University in Taichung. The environment for feeding animals is controlled at a room temperature (20 to 23° C.) and in a humidity of 50 to 60%, and the light cycles of day and night are maintained for 12 hours respectively. Experimental animals are allowed to eat and drink freely. All animal experiment procedures were carried out in accordance with the protocol approved by institutional animal care and use committee (IACUC) of Chung Shan Medical University.

Induction of Pancreatitis and Chemotherapy:

In order to induce acute pancreatitis in mice, Caerulein (25 μg/kg/h) were injected into the abdominal cavity of the mice by intraperitoneal (IP) injection every 7 hours 3 days before and 1 day before the experiment. The experimental mice were was divided into 4 groups. The chemotherapeutic drug of Gemcitabine was given with different concentrations (20, 50, 100, 200 mg/kg of body weight), and was administered by intraperitoneal injection for 4 consecutive weeks, once every 3 days, 10 times in total.

Experiments of the Probiotic Composition of the Present Disclosure:

Two strains of the *Lactobacillus paracasei* GMNL-133 and the *Lactobacillus reuteri* GMNL-89 were used in the experiment, respectively with the ratio of 1:0.1 (1.64×10$^7$ CFU/0.02 kg of body weight: 1.64×10$^6$ CFU/0.02 kg of body weight) and the ratio of 1:1 (1.64×10$^7$ CFU/0.02 kg of body weight: 1.64×10$^7$ CFU/0.02 kg of body weight). The dosage used is based on that 12.3 times the recommended daily intake per kilogram of body weight for humans is 1 time the dose for mice. The probiotic composition was fed into the stomach of the mice by tube feeding, 5 days a week, once a day, 0.2 mL each time.

Hematoxylin and Eosin Stain (H&E Stain) and Immunohistochemical Staining:

After the mice were sacrificed, the pancreas tissue was collected, fixed with formalin solution (TONYAR biotech. Inc., Taiwan), embedded in paraffin, tissue sectioned, and then subjected to H&E staining and immunohistochemical staining. Immunohistochemical staining was used to analyze the amount of the expressions of specific proteins such as Ki-67 (Anti-Ki67 antibody KO tested, Abcam, ab15580), vimentin ((D21H3) XP® Rabbit mAb, Cell Signaling Tech. #5741) in tumors.

Blood Analysis:

In order to study the adverse effects of the Caerulein, the chemotherapeutic drug of the Gemcitabine, and probiotic composition on serum biochemistry and blood cells, blood was collected after cardiac puncture in anesthetized mice, and the blood was immediately sent to Axel Biotechnology Inc. (Taichung) to perform blood tests and serum biochemical analysis.

Statistical Analysis:

The statistical software with SPSS version 10.1.3C (SPSS Inc., Chicago, Illinois, USA) is used for the statistical analysis to analyze the results. The data are expressed as mean±standard error (Mean±SD). The differences between the two groups are analyzed by Student's t-test, and the statistical results are regarded as statistical significance with $p<0.05$ (*).

Figure 2:
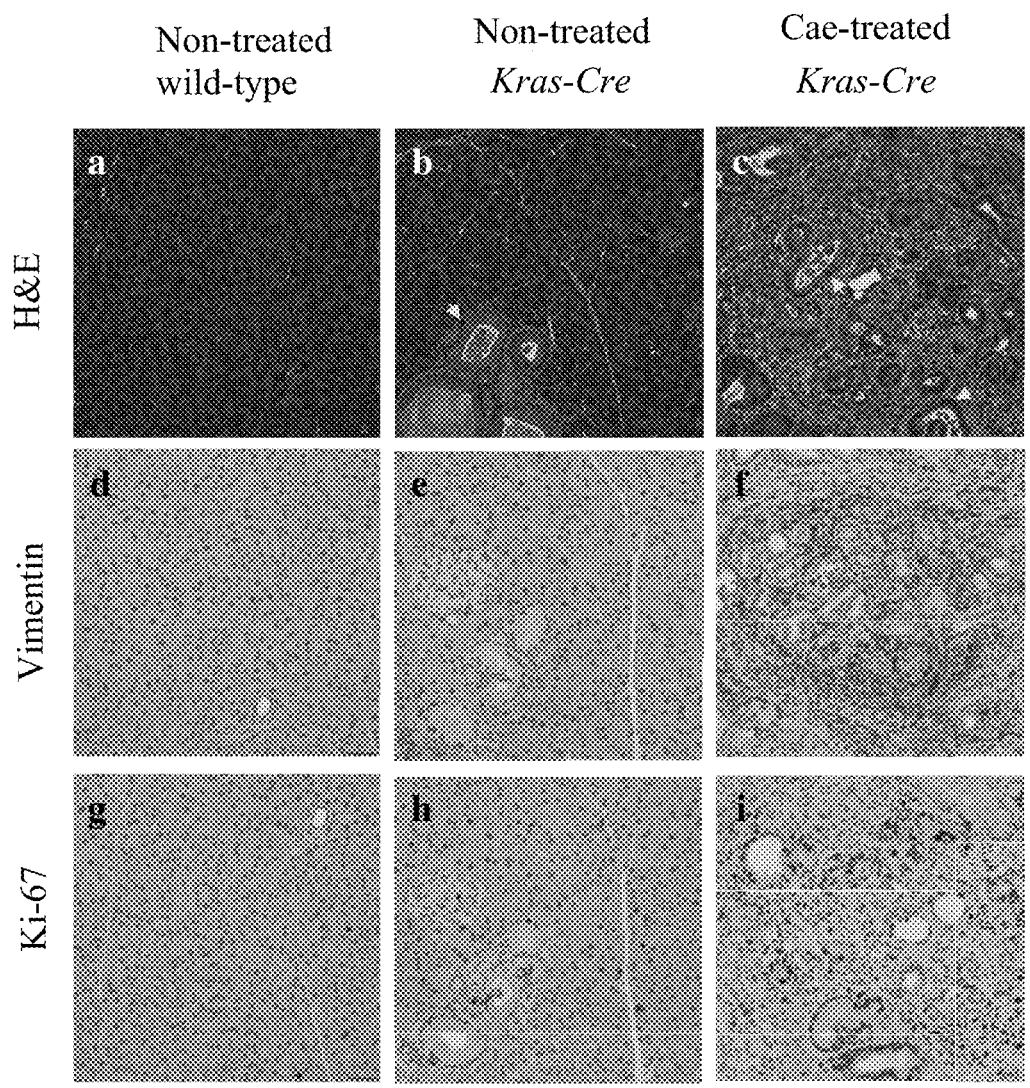
FIG. 2 shows in photographs results of histological staining of the pancreas of LSL-Kras$^{G12D/-}$-Pdx-1-Cre transgenic mice treated with Caerulein in the present experiment.

Experimental Result:

Establishment of a Mouse Model of Pancreatic Cancer:

FIG. 1 shows the process of establishment of a mouse model of pancreatic cancer. Compared with wild-type mice, pancreatic tissue sections (H&E staining) of $^{LSL-KrasG12D/-}$-Pdx-1-Cre (KC) gene transgenic mice show the enlarged nuclei (yellow arrows) in the reactive pancreatic duct cells (a and b in FIG. 2), the situation is obvious in the pancreas of the KC gene transgenic mice with pancreatic inflammation caused by Caerulein (c in FIG. 2). In addition, the vimentin related to the occurrence of pancreatic ductal adenocarcinoma show positive staining results in these pancreatic ducts and surrounding areas (e and f in FIG. 2). The cell proliferation marker of Ki67 also clearly appears in the pancreas of the untreated and Caerulein-treated KC gene transgenic mice (h and i in FIG. 2). According to the results of the above tissue staining, it is shown that the KC gene transgenic mice treated with Caerulein can induce pancreatic intraepithelial neoplasia lesions, which can be used as a mouse model of pancreatic ductal adenocarcinoma.

Figure 3:
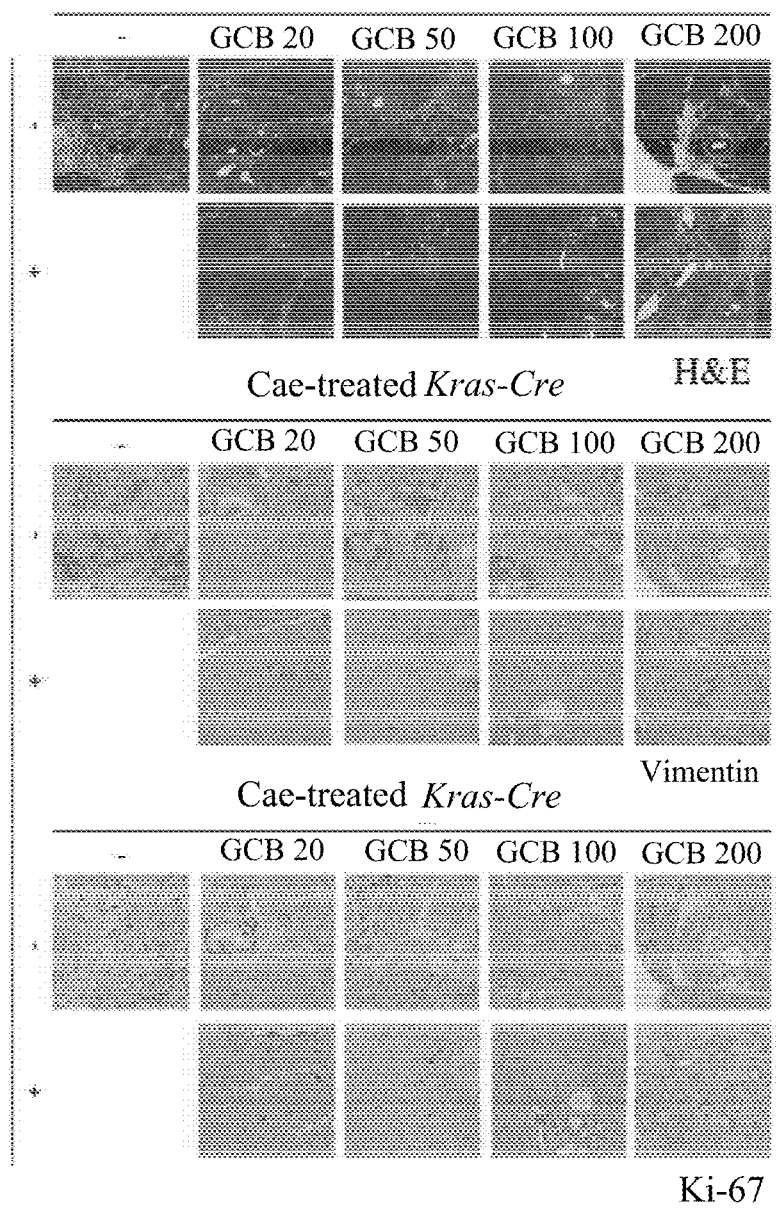
FIG. 3 shows in photographs results of histological staining of the pancreas of the Caerulein-treated LSL-Kras$^{G12D/-}$-Pdx-1-Cre transgenic mice treated with different concentrations of Gemcitabine alone or in combination with the probiotic composition of the present disclosure (with a ratio of the GMNL-133 to the GMNL-89 of 1:0.1) in the present experiment.

Treatments of the Chemotherapeutic Drug of the Gemcitabine:

FIG. 3 shows the tissue staining results of pancreas of the Caerulein-treated KC gene transgenic mice treated with different doses of the chemotherapeutic drug of Gemcitabine (20, 50, 100, 200 mg/kg). H&E staining results show that the pancreatic intraepithelial neoplasia lesion grades of the Gemcitabine-treated mice are lower than those of the untreated mice, and the expressions of the vimentin and the cell proliferation marker of Ki67 are also lower, in which two high-dose of the Gemcitabine, 100 mg/kg and 200 mg/kg, show excellent results.

The Probiotic Composition of the Present Disclosure Improves the Anticancer Effect of the Chemotherapeutic Drug of Gemcitabine:

Refer to FIG. 3, different doses of the chemotherapeutic drug of Gemcitabine combined with the probiotic composition (with the ratio of the GMNL-133 to the GMNL-89 of 1:0.1) is fed to treat the Caerulein-treated KC gene transgenic mice. The results of tissue staining show that the pancreatic intraepithelial neoplasia lesion grades of the mice treated with the Gemcitabine and the probiotic composition are significantly lower than those of the mice treated with the same dose of Gemcitabine alone. In addition, the expressions of the vimentin and the cell proliferation marker of Ki67 of the pancreas of the mice treated with the Gemcitabine and the probiotic composition are also significantly low.

Figure 4:
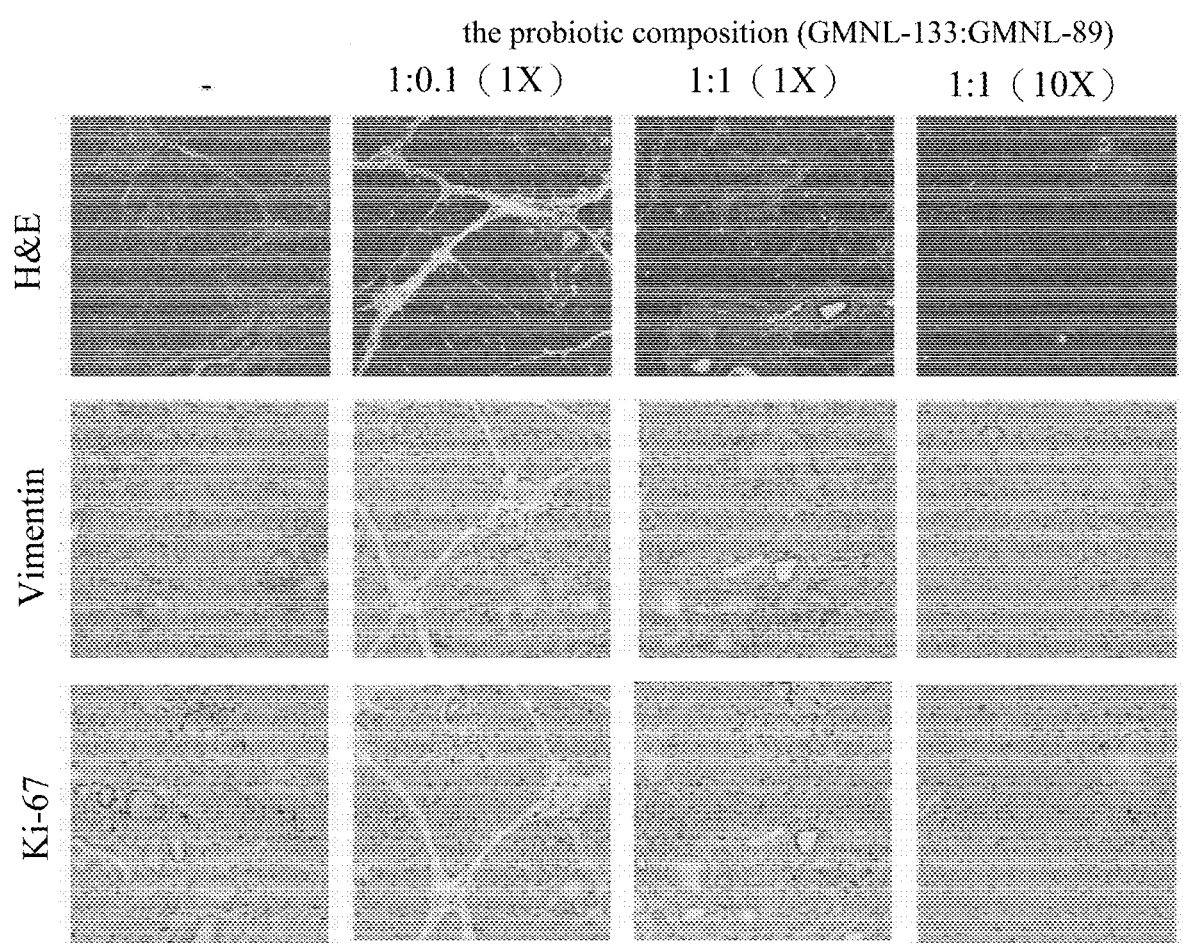
FIG. 4 shows in photographs results of histological staining of the pancreas of the Caerulein-treated LSL-Kras$^{G12D/-}$-Pdx-1-Cre transgenic mice treated with Gemcitabine in combination with different doses of the probiotic composition of the present disclosure in the present experiment.

In order to understand whether the ratio of the strains of the probiotic composition affects the results of pancreatic cancer treatment, a probiotic composition with a ratio of GMNL-133 to GMNL-89 of 1:1 and Gemcitabine were used to treat pancreatic cancer in mice. Refer to FIG. 4, the results of tissue staining show that the therapeutic effect for the ratio of the GMNL-133 to the GMNL-89 of 1:1 is worse than the therapeutic effect for the ratio of the GMNL-133 to the GMNL-89 of 1:0.1. However, when the feeding dose of the probiotic composition with the ratio of the GMNL-133 to the GMNL-89 of 1:1 is increased to 10 times, the best therapeutic effect can be achieved, in which the pancreatic intraepithelial neoplasia lesion grades and the expressions of the vimentin and the cell proliferation marker of Ki67 are the lowest compared with the above-mentioned experimental groups.

Figure 5:
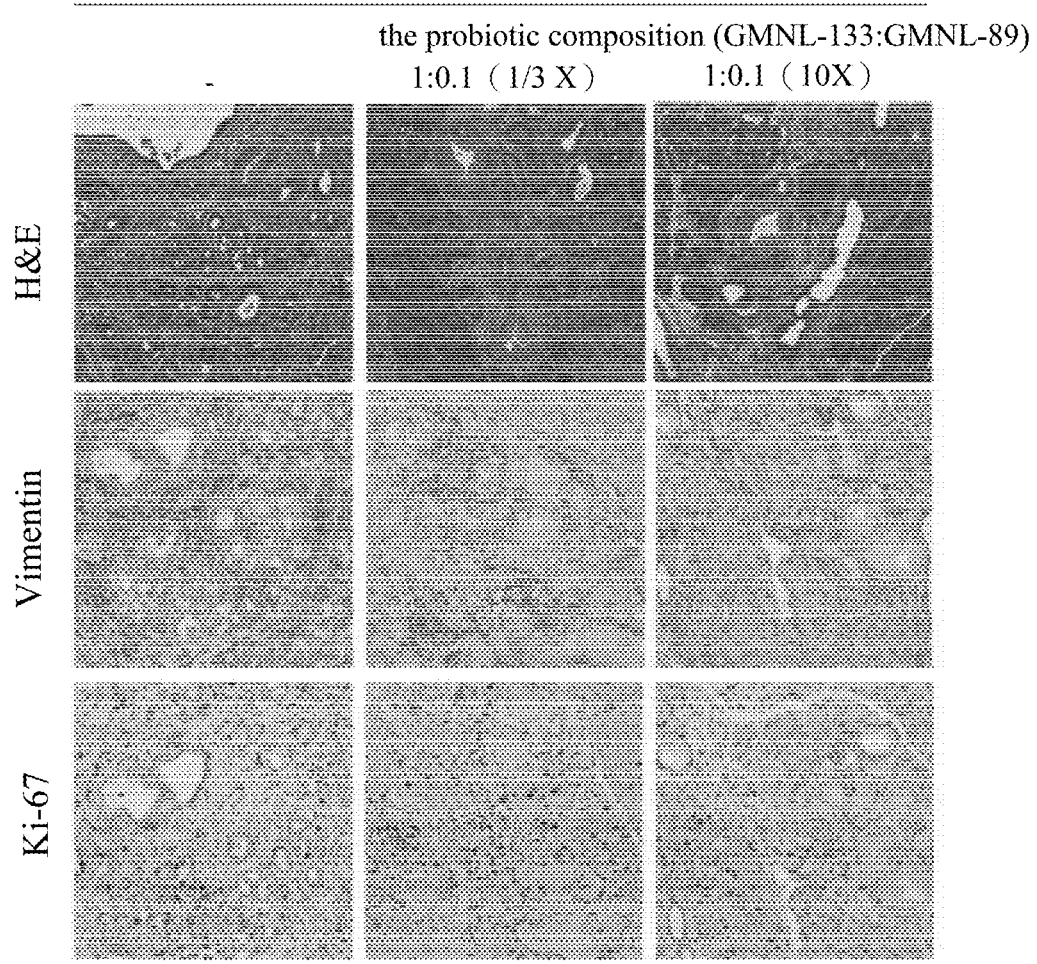
FIG. 5 shows in photographs results of histological staining of the pancreas of the Caerulein-treated LSL-Kras$^{G12D/-}$-Pdx-1-Cre transgenic mice treated with the probiotic composition of the present disclosure alone (with a ratio of the GMNL-133 to the GMNL-89 of 1:0.1) in the present experiment.

In addition, refer to FIG. 5, the Caerulein-treated KC gene transgenic mice were merely treated with the probiotic composition (with a ratio of the GMNL-133 to the GMNL-89 of 1:0.1). The results of tissue staining show that even without the chemotherapeutic drug of Gemcitabine, the probiotic composition at the high dose can still reduce the canceration of the pancreas, indicating that the probiotic composition of the present disclosure has the effect of treating pancreatic cancer.

Figure 6:
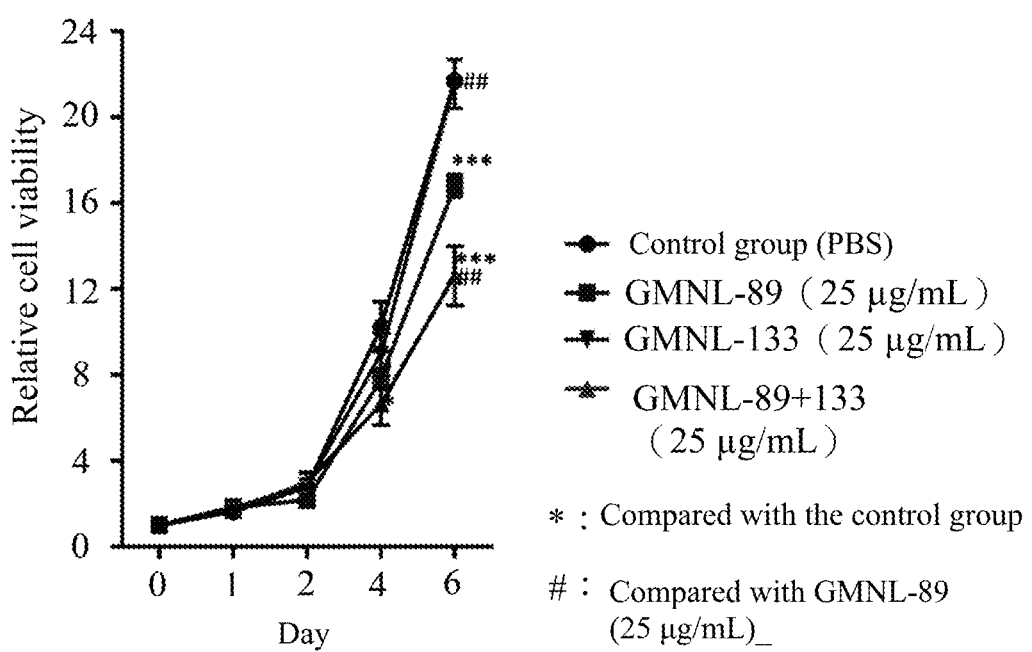
FIG. 6 is a graph showing the cell viability for BXPC-3 pancreatic cancer cells respectively treated with the GMNL- 89, the GMNL-133 and the probiotic composition of the present disclosure by the MTT (3-(4,5-Dimethylthiazol-2-yl)-2,5-diphenyltetrazolium bromide) test.
Figure 7A:
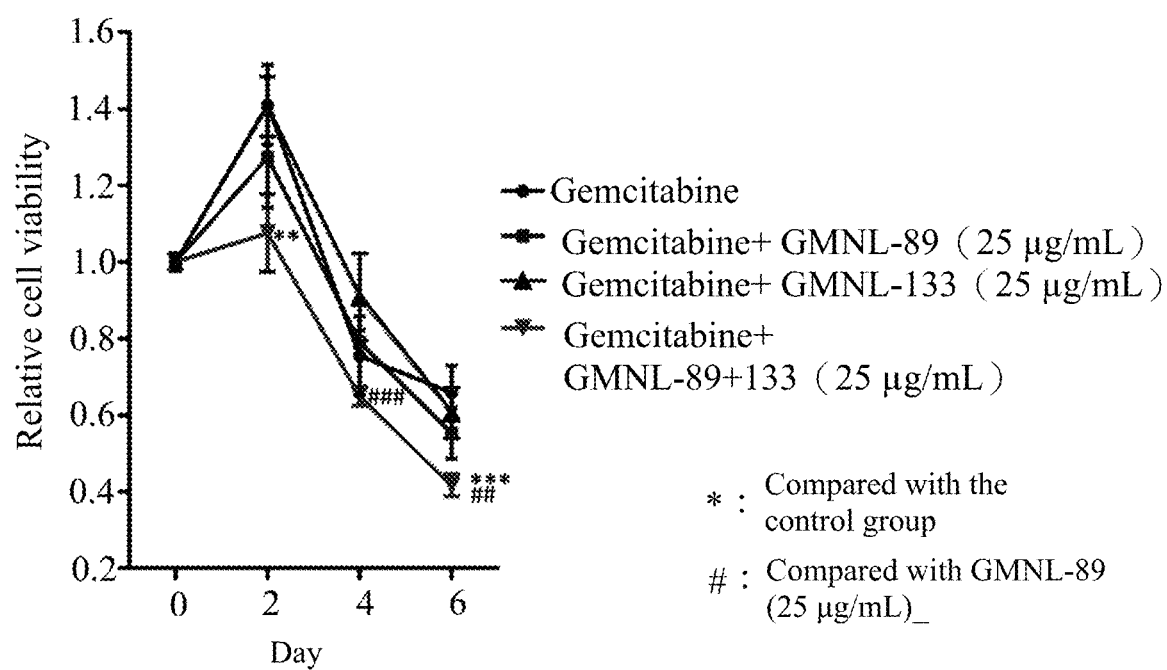
FIG. 7A is a graph showing the cell viability for BXPC-3 pancreatic cancer cells respectively treated with the GMNL-89 combined with Gemcitabine, GMNL-133 combined with Gemcitabine and the probiotic composition of the present disclosure combined with Gemcitabine by the MTT test.
Figure 7B:
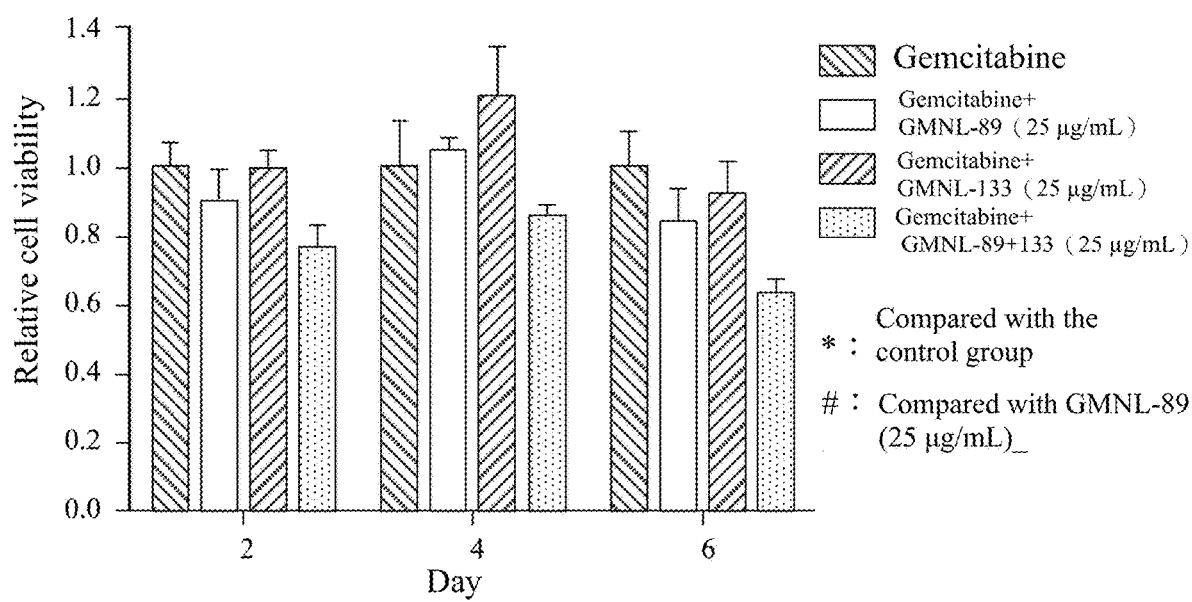
FIG. 7B is a bar graph showing the cell viability for BXPC-3 pancreatic cancer cells respectively treated with the GMNL-89 combined with Gemcitabine, GMNL-133 combined with Gemcitabine and the probiotic composition of the present disclosure combined with Gemcitabine by the MTT test.

Further, refer to FIGS. 6 to 7B, the MTT test (3-(4,5-Dimethylthiazol-2-yl)-2,5-diphenyltetrazolium bromide) is further used to detect the effect of the inhibition for the growth of cancer cells by the probiotic composition of the present disclosure combined with the Gemcitabine.

Experimental Method:

Experiment 1: the inhibitory effects on the growth of BXPC-3 pancreatic cancer cells by the *Lactobacillus reuteri* GMNL-89, the *Lactobacillus paracasei* GMNL-133, and the combination of the *Lactobacillus reuteri* GMNL-89 and the *Lactobacillus paracasei* GMNL-133 (i.e., the probiotic composition of the present disclosure):

2500 BXPC-3 pancreatic cancer cells were seeded into each well of a 96-well plate, and the 96-well plate was incubated at 37° C. overnight. After the old cell culture medium was aspirated, the fresh culture medium containing the lysate of the *Lactobacillus reuteri* GMNL-89, the lysate of the *Lactobacillus paracasei* GMNL-133 (25 ug/mL of concentration), or the lysate of the *Lactobacillus reuteri* G M N L-89 and the *Lactobacillus paracasei* G M N L-133 (i.e., the probiotic composition of the present disclosure) were respectively added to the BXPC-3 pancreatic cancer cells. Then, the BXPC-3 pancreatic cancer cells were cultured for 0 to 6 days. At different time points, based on day 0, the cell viability rate was determined by the MTT test, and the cell viability rate at different time points was calculated.

Experimental Results:

First, as shown in FIG. 6, the symbol "*" indicates that there is a statistical significance compared with the control group (phosphate buffered saline, PBS), and the more the number of "*" is, the greater the statistical significance between the two is. The symbol "#" indicates that there is a statistical significance compared with the GMNL-89 alone. On day 6, the treatment with the GMNL-89 alone significantly inhibited the growth of BXPC-3 pancreatic cancer cells, and there is a statistical significance. The treatment with the GMNL-133 alone has no effect on the growth of BXPC-3 pancreatic cancer cells. However, the combination of the GMNL-89 and the GMNL-133 (with a ratio of the GMNL-133 to the GMNL-89 of 1:1) can significantly inhibit the growth of BXPC-3 pancreatic cancer cells. The inhibitory effect caused by the combination of the GMNL-89 and the GMNL-133 is better than that caused by the GMNL-89 alone, and there is a statistical significance.

Experiment 2: The inhibitory effects on the growth of BXPC-3 pancreatic cancer cells by the *Lactobacillus reuteri* GMNL-89, the *Lactobacillus paracasei* GMNL-133, the combination of the *Lactobacillus reuteri* GMNL-89 and the *Lactobacillus paracasei* GMNL-133 (i.e., the probiotic composition of the present disclosure) respectively combined with the chemotherapeutic drug of Gemcitabine:

2500 BXPC-3 pancreatic cancer cells were seeded into each well of a 96-well plate, and the 96-well plate was incubated at 37° C. overnight. After the old cell culture medium was aspirated, the fresh culture medium containing the lysate of the *Lactobacillus reuteri* GMNL-89, the lysate of the *Lactobacillus paracasei* GMNL-133 (25 ug/mL of concentration), or the lysate of the *Lactobacillus reuteri* GMNL-89 and the *Lactobacillus paracasei* GMNL-133 (i.e., the probiotic composition of the present disclosure) were respectively mixed with the fresh culture medium containing the chemotherapeutic drug of Gemcitabine (10 ng/mL of concentration) to be added to the BXPC-3 pancreatic cancer cells. Then, the BXPC-3 pancreatic cancer cells were cultured for 0 to 6 days. At different time points, based on day 0, the cell viability rate was determined by the MTT test, and the cell viability rate at different time points was calculated.

Experimental Results:

First, as shown in FIG. 7A and FIG. 7B, the symbol "*" indicates that there is a statistical significance compared with the chemotherapeutic drug of Gemcitabine (control group), and the more the number of "*" is, the greater the statistical significance between the two is. The symbol "#" indicates that there is a statistical significance compared with the GMNL-89. As shown in FIG. 7A, the Gemcitabine caused the death of the BXPC-3 pancreatic cancer cells from the second day, and the cell viability rate reached the lowest on the sixth day. Compared with the treatment with the Gemcitabine alone, the treatment with the Gemcitabine and the GMNL-89 can lead to more death of BXPC-3 pancreatic cancer cells. The GMNL-133 has no effect on the death of BXPC-3 pancreatic cancer cells caused by the Gemcitabine. The combination of the Gemcitabine, the GMNL-89 and the GMNL-133 can cause more BXPC-3 pancreatic cancer cell death than the combination of the Gemcitabine and the GMNL-89, and there is a statistical significance. Furthermore, as shown in FIG. 7B, based on the Gemcitabine at each time point, the combined use of the Gemcitabine and the probiotic composition of the present disclosure (with a ratio of the GMNL-133 to the GMNL-89 of 1:1) can reduce 24%, 14%, and 37% of the viability rate of the BXPC-3 pancreatic cancer cells respectively, and there is a statistical significance. According to the above results, the probiotic composition of the present disclosure can improve the effect of the chemotherapeutic drug of the Gemcitabine on killing the BXPC-3 pancreatic cancer cells.

The Probiotic Composition Improves the Side Effects of the Chemotherapeutic Drug of Gemcitabine:

Common side effects of the chemotherapeutic drug of Gemcitabine include anemia, low white blood cell count, low platelet count, increased liver function index, weight loss, fever, constipation, diarrhea, hematuria, increased creatinine and so on. The following table 1 shows the serum biochemical and blood cell analysis of the Caerulein treated LSL-Kras$^{G12D/-}$-Pdx-1-Cre transgenic mice treated with the chemotherapeutic drug of Gemcitabine and different doses of the probiotic composition (GMNL-133: GMNL-89=1:1).

TABLE 1

|  | Non-treated KC | Cae-GCB 200 KC | Cae-GCB 200 + Probiotic Composition (GMNL-133:GMNL-89 = 1:1 (1X)) KC | Cae-GCB 200 + Probiotic composition (GMNL-133:GMNL-89 = 1:1 (10X)) KC |
|---|---|---|---|---|
| Body weight (g) | 29.78 ± 1.81 | 21.10 ± 1.44 | 20.30 ± 1.70 | 25.80 ± 2.46 |
| Gastrocnemius muscle weight (g) | 0.18 ± 0.04 | 0.13 ± 0.00 | 0.29 ± 0.21 | 0.39 ± 0.04 |
| Red blood cell (M/μL) | 9.46 ± 1.18 | 8.70 | 7.11 ± 1.55 | 7.55 ± 1.52 |
| Platelets (K/μL) | 808.00 ± 232.50 | 1222.00 | 576.75 ± 805.04 | 801.45 ± 1123.66 |
| White blood cell (K/μL) | 7.79 ± 1.72 | 3.04 | 3.09 ± 3.29 | 5.94 ± 7.33 |
| AST (md/dL) | 62.67 ± 10.02 | 351.00 | 222.75 ± 120.82 | 127.67 ± 80.15 |
| ALT (md/dL) | 20.00 ± 6.08 | 60.00 | 59.75 ± 12.53 | 36.00 ± 21.17 |

As shown in Table 1, the chemotherapeutic drug of Gemcitabine caused the KC gene transgenic mice treated with Caerulein (25 μg/kg) to lose weight and muscle (gastrocnemius) weight significantly. The problem of low white blood cell count caused by the chemotherapeutic drug of Gemcitabine can be improved by taking the probiotic composition of the present disclosure (recovering the number of white blood cells), so as to increase the immunity of mice undergoing chemotherapy. When the chemotherapeutic drug is used in combination with the probiotic composition of the present disclosure (with a ratio of the GMNL-133 to the GMNL-89 of 1:1) to treat pancreatic cancer in mice, the body weight and muscle weight of the mice are significantly increased. The results of biochemical tests show that the liver function index of the Aspartate Transaminase (AST) and the Alanine aminotransferase (ALT) of the KC gene transgenic mice treated with Caerulein (25 μg/kg) which were only treated with the chemotherapeutic drug of Gemcitabine are prone to elevate, and thus liver inflammation occurs. When the chemotherapeutic drug is used in combination with the probiotic composition of the present disclosure (with a ratio of the GMNL-133 to the GMNL-89 of 1:1) to treat pancreatic cancer in mice, the liver function index of AST and ALT of the mice are both significantly decreased. In addition, the higher the dosage of the composition is, the better the effect is.

In view of the above blood biochemical analysis and blood cell count results, the probiotic composition of the present disclosure can effectively improve the side effects caused by the chemotherapy drug of Gemcitabine in the treatment of pancreatic cancer, and can increase body weight, muscle weight, white blood cells, and reduce liver function index AST and ALT.

While the preferred embodiments of the present disclosure have been described above, it will be recognized and understood that various changes and modifications can be made, and the appended claims are intended to cover all such changes and modifications which may fall within the spirit and scope of the present disclosure.

What is claimed is:

1. A method for improving a side effect of Gemcitabine, comprising a step of administering a probiotic composition comprising an effective amount of *Lactobacillus paracasei* GMNL-133, an effective amount of *Lactobacillus reuteri* GMNL-89, and a pharmaceutically acceptable carrier to a subject in need, wherein the side effect is liver inflammation, and the *Lactobacillus paracasei* GMNL-133 was deposited in the China Center for Type Culture Collection located at Wuhan University, Wuhan 430072 P.R. China on Sep. 26, 2011 under an accession number CCTCC NO. M 2011331 under the Budapest Treaty, and the *Lactobacillus reuteri* GMNL-89 was deposited in the China Center for Type Culture Collection located at Wuhan University, Wuhan 430072 P.R. China on Nov. 19, 2007 under an accession number CCTCC NO. M 207154 under the Budapest Treaty, wherein a ratio of a number of bacteria of the *Lactobacillus paracasei* GMNL-133 to a number of bacteria of the *Lactobacillus reuteri* GMNL-89 is 1:1.

2. The method of claim 1, wherein the *Lactobacillus paracasei* GMNL-133 in the probiotic composition is administered at a dose of $4\times10^9$ to $4\times10^{10}$ cfu/60 kg of body weight per day to a subject in need of improving the side effect of Gemcitabine, and the *Lactobacillus reuteri* GMNL-89 in the probiotic composition is administered at a dose of $4\times10^9$ to $4\times10^{10}$ cfu/60 kg of body weight per day to the subject in need of improving the side effect of Gemcitabine.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Forward primer(PAF)

<400> SEQUENCE: 1
agagtttgat cctggctcag                                                 20

<210> SEQ ID NO 2
<211> LENGTH: 18
<212> TYPE: DNA
<213> ORGANISM: Artificial Sequence
<220> FEATURE:
<223> OTHER INFORMATION: Forward primer(536R)

<400> SEQUENCE: 2
gtattaccgc ggctgctg                                                   18

<210> SEQ ID NO 3
<211> LENGTH: 521
<212> TYPE: DNA
<213> ORGANISM: Artificial Sequence

```
<220> FEATURE:
<223> OTHER INFORMATION: Lactobacillus paracasei 16S rDNA partial
      sequence

<400> SEQUENCE: 3
tctgcggtgc ctatacatgc aagtcgtacg cactggccca actgattgat ggtgcttgca      60
cctgattgac gatggatcac cagtgagtgg cggacgggtg agtaacacgt aggtaacctg     120
ccccggagcg ggggataaca tttggaaaca gatgctaata ccgcataaca acaaaagcca     180
catggctttt gtttgaaaga tggctttggc tatcactctg ggatggacct gcggtgcatt     240
agctagttgg taaggtaacg gcttaccaag gcgatgatgc atagccgagt tgagagactg     300
atcggccaca atggaactga gacacggtcc atactcctac gggaggcagc agtagggaat     360
cttccacaat gggcgcaagc ctgatggagc aacaccgcgt gagtgaagaa gggtttcggc     420
tcgtaaagct ctgttgttgg agaagaacgt gcgtgagagt aactgttcac gcagtgacgg     480
tatccaacca gaaagtcacg gctaactacg tgccagatgg g                         521

<210> SEQ ID NO 4
<211> LENGTH: 521
<212> TYPE: DNA
<213> ORGANISM: Artificial Sequence
<220> FEATURE:
<223> OTHER INFORMATION: Lactobacillus reuteri 16S rDNA sequence

<400> SEQUENCE: 4
tctgcggtgc ctatacatgc aagtcgtacg cactggccca actgattgat ggtgcttgca      60
cctgattgac gatggatcac cagtgagtgg cggacgggtg agtaacacgt aggtaacctg     120
ccccggagcg ggggataaca tttggaaaca gatgctaata ccgcataaca acaaaagcca     180
catggctttt gtttgaaaga tggctttggc tatcactctg ggatggacct gcggtgcatt     240
agctagttgg taaggtaacg gcttaccaag gcgatgatgc atagccgagt tgagagactg     300
atcggccaca atggaactga gacacggtcc atactcctac gggaggcagc agtagggaat     360
cttccacaat gggcgcaagc ctgatggagc aacaccgcgt gagtgaagaa gggtttcggc     420
tcgtaaagct ctgttgttgg agaagaacgt gcgtgagagt aactgttcac gcagtgacgg     480
tatccaacca gaaagtcacg gctaactacg tgccagatgg g                         521
```